United States Patent [19]

Takahashi et al.

[11] Patent Number: 4,994,600
[45] Date of Patent: Feb. 19, 1991

[54] PROCESS FOR PREPARING TRANS-BETA-BENZOYLACRYLIC ACID ESTER

[75] Inventors: Satomi Takahashi, Kobe; Yasuyoshi Ueda, Takasago; Yoshifumi Yanagida; Namito Yoshio, both of Takasago; Takehisa Ohashi, Kobe; Kiyoshi Watanabe, Akashi, all of Japan

[73] Assignee: Kanegafuchi, Kagaku, Kogyo, Kabushiki, Kaisha, Osaka, Japan

[21] Appl. No.: 869,782

[22] Filed: Jun. 2, 1986

[30] Foreign Application Priority Data

Jun. 5, 1985 [JP] Japan ................. 60-122301

[51] Int. Cl.$^5$ .............. C07C 67/08; C07C 67/327; C07C 67/333; C07C 69/738
[52] U.S. Cl. .................... 560/051; 560/53
[58] Field of Search .................... 560/51, 53

[56] References Cited

U.S. PATENT DOCUMENTS 4,562,068 12/1985 Moller et al. ................. 560/51

FOREIGN PATENT DOCUMENTS 2107714 5/1983 United Kingdom ................. 560/51

OTHER PUBLICATIONS

Nippon Kagakukaishi, 88, 224 (1967).
Price, J. Amer. Chem. Soc., 45, 222 (1923).
Sujiyama et al., Bull. Chem. Soc. Japan, 42, 1353 (1969).
Delaby et al., Bull. Soc. Chim. France, 2061 to 2064 (1961).

Primary Examiner—Vivian Garner
Attorney, Agent, or Firm—Armstrong, Nikaido, Marmelstein, Kubovcik & Murray

[57] ABSTRACT

A process for preparing trans-$\beta$-benzoylacrylic acid ester having the general formula (I):

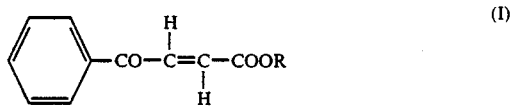

wherein R is alkyl group or aralkyl group, which comprises dealcoholizing $\beta$-benzoyl-$\alpha$-alkoxypropionic acid ester having the general formula (II):

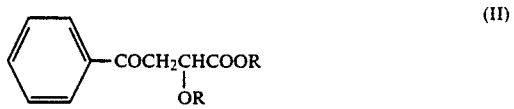

wherein R is above, in the presence of an acid catalyst to give trans-$\beta$-benzoylacrylic acid ester having the general formula (I).

According to the process of the present invention, the by-product (II) produced in the esterification reaction of $\beta$-benzoylacrylic acid (III) with the alcohol (V) by the dehydration reaction can be converted into the compound (I) by the dealcoholization reaction in the presence of the acid catalyst and thus trans-$\beta$-benzoylacrylic acid ester (I) with a high purity can be produced in an industrially advantageous manner.

11 Claims, No Drawings

PROCESS FOR PREPARING TRANS-BETA-BENZOYLACRYLIC ACID ESTER

BACKGROUND OF THE INVENTION

The present invention relates to a process for preparing trans-β-benzoylacrylic acid ester having the general formula (I):

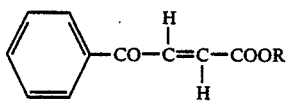
(I)

wherein R is an alkyl group or aralkyl group. The purpose of the present invention is to provide a process for preparing the compound (I) in an industrially advantageous manner, the compound (I) being an important intermediate compound for the production of the medicines and the perfumes.

Hitherto, the most commonly known method for synthesizing the ester has been the method by the dehydration reaction between carboxylic acid and alcohol. This method has been used for synthesizing β-benzoylacrylic acid ester, for example, ethyl β-benzoylacrylate. In case of the dehydration reaction between β-benzoylacrylic acid and ethanol, though it has been reported that ethyl β-benzoylacrylate is obtained with a good yield, geometrical isomerism, i.e. cis-form and trans-form, of the starting material and of the product as well as the concrete procedure have not been described [Nippon Kagakukaishi, 88, 224 (1967)]. On the contrary, other report describes that the product of the ethyl-esterification reaction of β-benzoylacrylic acid with ethanol is hardly purified [J. Amer. Chem. Soc., 45, 222 (1923)], while another report describes that ethyl β-benzoyl-α-ethoxypropionate was obtained in the usual ethyl-esterification reaction [Bull. Chem. Soc. Japan, 42, 1353 (1969)]. Therefore, the above-mentioned method for synthesizing β-benzoylacrylic acid ester by the dehydration reaction between 8-benzoylacrylic acid and alcohol is not suited for the method for industrially effective production of β-benzoylacrylic acid ester since it has various problems to be solved such as unclearness of geometric isomerism of the product, of a kind of the products and of a quantitative ratio of the products. Under such circumstances, several different methods for preparing trans-β-benzoylacrylic acid ester have been studied by many research workers. For example, a method by the aldol condensation reaction between acetophenone and glyoxylic acid ester (Japanese Unexamined Patent Publication No. 192622/1982) and a method by halogenating β-benzoylpropionic acid ester and then dehydrohalogenating the resultant [J. Amer. Chem. Soc., 45, 222 (1923)] have been proposed. However, these methods are also disadvantageous for an industrial application since, in the former method, the product is not easily produced and very expensive glyoxylic acid ester is employed and, in the latter method, the reaction is carried out in a multiple step including a preparation of β-benzoylpropionic acid ester and the yield is low. Also a method by esterifying trans-β-benzoylacrylic acid by means of dialkyl sulfate or halogenated alkyl is not suited for the industrial production since it has various drawbacks such as noxious reaction agent and liquid-waste treatment after the reaction.

In order to establish the industrial process for preparing trans-β-benzoylacrylic acid ester endowed with excellent operability, safety and economical advantage, the present inventors have studied a condition for predominantly producing trans-form of the ester and suppressing the by-product in the reaction between β-benzoylacrylic acid and alcohol.

As the result of the continuous effort of the present inventors, now it has been found that in the esterification reaction of β-benzoylacrylic acid having the formula (III):

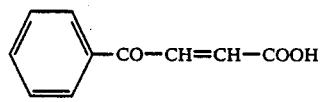
(III)

with the alcohol having the general formula (V):

ROH (V)

wherein R is as above, by the dehydration reaction, considerable amount of β-benzoyl-α-alkoxypropionic acid ester having the general formula (II):

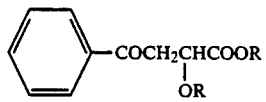
(II)

wherein R is as above, is by-produced in addition to desired trans-β-benzoylacrylic acid ester having the general formula (I):

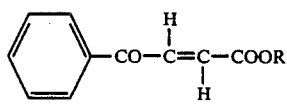
(I)

wherein R is as above, and that the by-product (II) can be easily converted into the desired compound (I) by the dealcoholization reaction in the presence of an acid catalyst.

SUMMARY OF THE INVENTION

According to the present invention, there is provided a process for preparing trans-β-benzoylacrylic acid ester having the general formula (I):

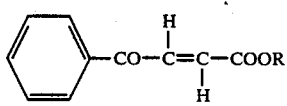
(I)

wherein R is an alkyl group or aralkyl group, which comprises dealcoholizing β-benzoyl-α-alkoxypropionic acid ester having the general formula (II):

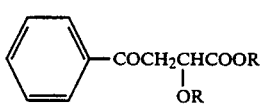
(II)

wherein R is as above, in the presence of an acid catalyst. According to the process of the present invention, the by-product (II) produced in the esterification reaction of β-benzoylacrylic acid (III) with the alcohol (V) by the dehydration reaction can be converted into the compound (I) by the dealcoholization reaction in the presence of the acid catalyst and thus trans-β-benzoylacrylic acid ester (I) with a high purity can be produced in an industrially advantageous manner.

DETAILED DESCRIPTION OF THE INVENTION

The process of the present invention is illustrated in the following reaction scheme.

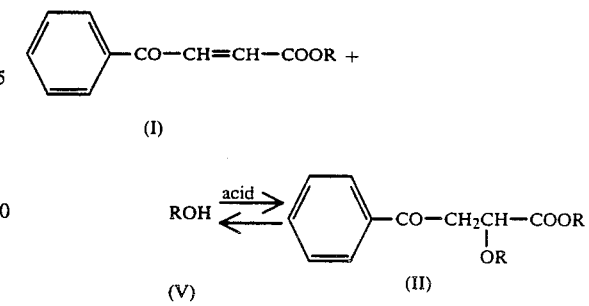

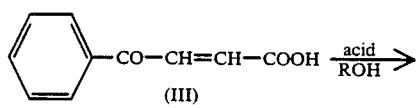

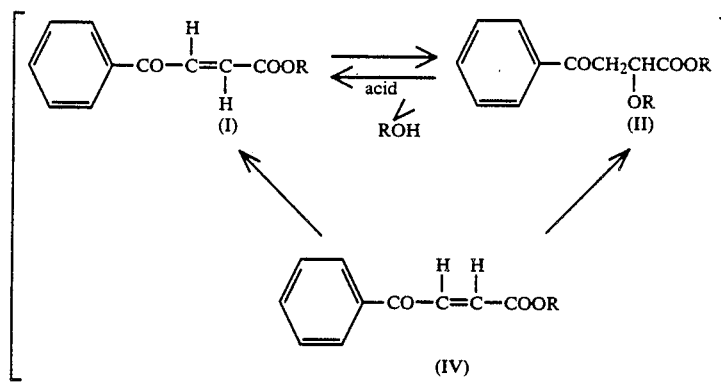

In the above reaction scheme, R is as above, the compound (III) is trans-form, cis-form or a mixture thereof of β-benzoylacrylic acid.

In the dehydration reaction between trans-β-benzoylacrylic acid (III) and the alcohol, both desired trans-β-benzoylacrylic acid ester (I) and a considerable amount of the alcohol addition product, β-benzoyl-α-alkoxypropionic acid ester (II), as the by-product are produced as shown in the following scheme.

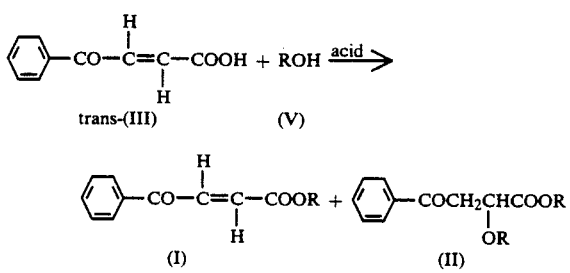

Hitherto, this by-production of the alcohol addition product has been an obstacle for effectively producing the desired compound (I) with a high purity.

However, now it has been found that the desired compound (I) and the alcohol addition product (II) are mutually conversible and they are in equilibrium with each other under control of a concentration of the alcohol as shown in the following reaction scheme.

The removal of the alcohol (V) from the reaction system in the presence of an acid catalyst shifts the equilibrium to the desired compound (I), finally the compound (II) being quantitatively converted into the compound (I), and thus the desired compound (I) can be obtained with a high purity in an extremely easy way.

In this way, the compound (II) can be converted into the desired compound (I) by the acid catalyst at room temperature or under heating. However, if the produced alcohol is not removed from the reaction system, the conversion of the compound (II) into the desired compound (I) becomes incomplete. When the equilibrium is shifted to the desired compound (I) by, for example, distilling away the produced alcohol under normal or reduced pressure, the desired compound (I) can be effectively obtained.

In case that the same esterification reaction is carried out on cis-β-benzoylacrylic acid (III), cis-β-benzoylacrylic acid ester (IV), trans-β-benzoylacrylic acid ester (I) and the alcohol addition product (II) are obtained as shown in the following reaction scheme.

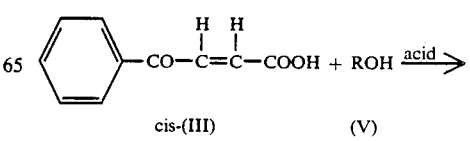

(I) + (II) + 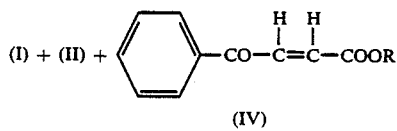

(IV)

In the above reaction, the side-produced alcohol addition product (II) can be converted into the desired compound (I) as mentioned above. It was found that the concurrently produced compound (IV) can be easily isomerized into the desired trans-β-benzoylacrylic acid ester (I) by the acid catalyst under the same reaction condition as in case of the dealcoholization reaction.

From the practical point of view, the esterification reaction is preferably conducted while removing water produced as the reaction proceeds from the reaction system together with an azeotropic solvent in a conventional manner so that the equilibrium is shifted to the esterification.

Further, when β-benzoylacrylic acid is esterified with around stoichiometric amount (for example, 1.0 to 1.5 equivalent amount) of the alcohol while removing water by means of the azeotropic solvent, the esterification (dehydration) reaction proceeds effectively through removal of produced water and at the same time a decreased concentration of the alcohol in the reaction system accelerates the conversion of the alcohol addition product into the desired compound as shown in the following reaction scheme.

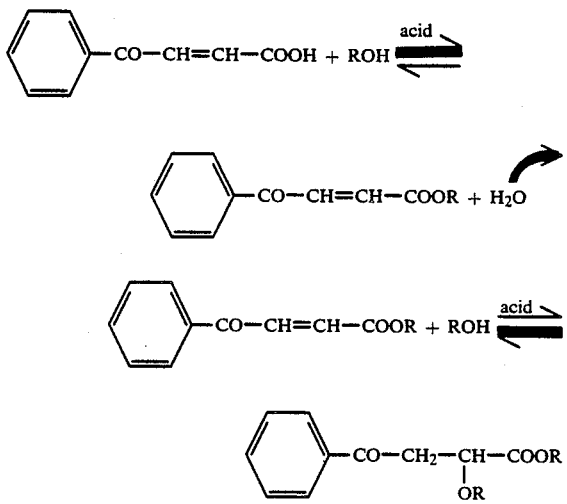

In this manner, by-production and accumulation of the alcohol addition product is surpressed and thus the desired compound (I) can be efficiently obtained.

When cis-β-benzoylacrylic acid is employed, the by-produced compound (IV) is isomerized into the desired compound (I) as mentioned above.

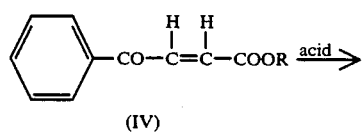

(IV)

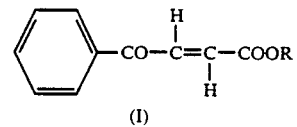

(I)

Therefore, according to the present invention, any β-benzoylacrylic acid in trans-form, in cis-form or in a mixture thereof can be converted into trans-β-benzoylacrylic acid ester with an extremely high purity.

As mentioned above, in the process for preparing trans-β-benzoylacrylic acid ester by the esterification reaction between β-benzoylacrylic acid and alcohol, the process of the present invention is characterized in that the by-product and cis-isomer are converted into the desired compound by distilling away the alcohol which constitutes β-benzoyl-α-alkoxypropionic acid ester in the presence of the acid catalyst.

In the conversion reaction of the compound (II) or of the compound (IV) into the desired compound (I), examples of the substituent R are a linear alkyl group such as methyl group, ethyl group, n-propyl group, n-hexyl group or n-octyl group; a branched alkyl group such as isopropyl group, isobutyl group or isoamyl group; a cycloalkyl group such as cyclohexyl group; an aralkyl group such as β-phenylethyl group.

The conversion reaction of the compound (II) or of the compound (IV) into the desired compound (I) can be conducted without solvent or in an inert solvent such as benzene or toluene. The reaction solvent may be benzene, toluene or the like in a single form or may be a mixed solvent containing other solvent without interfering with the proceeding of the reaction together with benzene, toluene or the like as a main solvent. Examples of the acid present in the reaction system are, for example, an inorganic acid such as sulfuric acid or hydrochloric acid, an organic acid such as paratoluenesulfonic acid, Lewis acid such as boron trifluoride etherate, and the like. Though the reaction temperature may range from 20° to 150° C., it is preferably not less than 40° C. from the view point of the reaction rate, and preferably not more than 100° C. from the view point of decomposition or coloration of the product. An amount of the acid is generally 0.02 to 40 % (W/V) based on the reaction mixture in case of a non-volatile acid such as paratoluenesulfonic acid, or 10 to 50 % (W/V) in case of a volatile solvent such as hydrochloric acid. The reaction is usually carried out for the time ranging from a few minutes to about 5 hours.

The proceeding of the reaction can be followed by means of a thin layer chromatography. After completion of the reaction, desired trans-β-benzoylacrylic acid ester (I) can be obtained by extraction or distillation.

In the conversion reaction, the alcohol addition product (II) and cis-β-benzoylacrylic acid ester can be separately or simultaneously converted into the desired compound (I). Trans-form of β-benzoylacrylic acid (III) is reacted with the alcohol in the presence of the acid to produce the compounds (I) and (II) or, if cis-form of β-benzoylacrylic acid is employed, to produce the compounds (I), (II) and (IV) in the reaction system and then the compound (II) and/or the compound (IV) are converted into the desired compound (I) while distilling away the excessive unreacted alcohol and the alcohol produced in the conversion reaction from the reaction system under normal or reduced pressure, finally only the desired compound (I) being isolated.

In the esterification (dehydration) reaction between β-benzoylacrylic acid and the alcohol employing the azeotropic solvent, an amount of the alcohol is preferably about 1.0 to about 1.5 equivalent amount based on β-benzoylacrylic acid with consideration of remaining β-benzoylacrylic acid and by-produced β-benzoyl-α-alkoxypropionic acid ester. Benzene, chloroform, 1,1,1-trichloroethane or the like can be employed as the azeotropic solvent in the usual way. A kind of the acid present in the reaction system and an amount of the acid are as mentioned above. The reaction is carried out for the time ranging from about 1 hour to 5 hours. After completion of the reaction, desired trans-β-benzoylacrylic acid ester (I) can be obtained by extraction or distillation.

Any β-benzoylacrylic acid can be employed in cis-form, in trans-form or in a mixture thereof.

The present invention is more particularly described by the following Examples and Reference Example. However, it should be understood that the present invention is not limited to the Examples and the Reference Example and various changes and modifications can be made without departing from the scope and spirit of the present invention.

EXAMPLE 1

A mixture of 268 mg of methyl β-benzoyl-α-methoxypropionate, 150 mg of paratoluenesulfonic acid monohydrate and 5 ml of toluene was stirred at 80° C. for 1 hour. A pressure was reduced with an aspirator and a total amount of the resultant was reduced to ½ by concentration. The resultant was stirred at 80° C. for 20 minutes and was left for cooling. The reaction mixture was distributed between ethyl acetate and water and the ethyl acetate layer was washed with a saturated solution of $NaHCO_3$ and then with water, and was dried with anhydrous magnesium sulfate. The solvent was distilled away to give 206 mg of methyl trans-β-benzoylacrylate as a yellow oil.

$^1H$ NMR ($CDCl_3$,δ): 8.15 to 7.32 (m, phenyl), 7.95 (d, olefinic proton), 6.88 (d, olefinic proton) and 3.85 (s, ester methyl).

EXAMPLE 2

A mixture of 6.45 g of ethyl trans-β-benzoylacrylate, 3.55 g of ethyl β-benzoyl-α-ethoxypropionate and 1.80 g of sulfuric acid was stirred at 100° C. while reducing the pressure to 20 mmHg with the aspirator and distilling away produced ethanol. The reaction was continued for 10 minutes and then cooled, followed by the procedure as in Example 1 to give 7.76 g of ethyl trans-β-benzoylacrylate.

EXAMPLE 3

A mixture of 6.79 g of ethyl trans-β-benzoylacrylate, 1.97 g of ethyl β-benzoyl-α-ethoxypropionate and 0.12 g of sulfuric acid was subjected to distillation under reduced pressure. 7.02 g of ethyl trans-8-benzoylacrylate was distilled out at 123 to 134° C./3 mmHg.

EXAMPLE 4

A mixture of 7.75 g of trans-β-benzoylacrylic acid, 25.8 ml of ethanol and 1.63 g of sulfuric acid was stirred at 62° C. for 3 hours. A pressure was gradually reduced with the aspirator and ethanol was distilled away for 20 minutes. After a pressure was finally reduced to 20 mmHg, the resultant was stirred at 62° C. for 1.5 hours and then cooled, followed by the procedure as in Example 1 to give 8.18 g of ethyl trans-β-benzoylacrylate.

EXAMPLE 5

A mixture of 5.00 g of trans-β-benzoylacrylic acid, 1.67 ml of n-propanol and 1.05 g of sulfuric acid was stirred at 100° C. for 1.5 hours. A pressure was gradually reduced with the aspirator and n-propanol was distilled away for 15 minutes. After a pressure was finally reduced to 20 mmHg, the resultant was stirred at 100° C. for 10 minutes and then cooled, followed by the procedure as in Example 1 to give 5.78 g of n-propyl trans-β-benzoylacrylate.

$^1H$ NMR ($CDCL_3$,δ): 8.13 to 7.33 (m, phenyl), 7.94 (d, olefinic proton), 6.88 (d, olefinic proton), 4.20 (t, $-OCH_2CH_2CH_3$, methylene), 2.77 (m, $-OCH_2CH_2CH_3$, methylene) and 1.00 (t, $-OCH_2CH_2CH_3$, methyl)

EXAMPLE 6

A mixture of 200 mg of ethyl cis-β-benzoylacrylate, 200 mg of boron trifluoride etherate (about 47 %) and 10 ml of toluene was stirred at 80° C. for 45 minutes and then cooled, followed by the procedure as in Example 1 to give 175 mg of ethyl trans-β-benzoylacrylate as a yellow oil.

$^1H$ NMR ($CDCl_3$, δ):
8.10 to 7.35 (m, phenyl), 7.90 (d, olefinic
proton), 6.85 (d, olefinic proton), 4.28 (q, —OEt, methylene) and 1.33 (t, —OEt, methyl).

EXAMPLE 7

A mixture of 3.00 g of β-benzoylacrylic acid (cis-/trans = ½ according to $^1H$ NMR analysis), 10 ml of ethanol and 0.63 g of sulfuric acid was refluxed for 2 hours. A pressure was gradually reduced with the aspirator and ethanol was distilled away for 10 minutes. After a pressure was finally reduced to 20 mmHg, the resultant was stirred at 85° C. for 40 minutes and then cooled, followed by the procedure as in Example 1 to give 2.45 g of ethyl trans-β-benzoylacrylate.

EXAMPLE 8

A mixture of 7.50 g of trans-β-benzoylacrylic acid, 2.36 g of ethanol, 0.50 g of sulfuric acid and 30 ml of chloroform was refluxed for 5 hours while azeotropically removing water produced from the reaction system. After cooling, the reaction mixture was washed with a saturated solution of NaHCO and then with water. The solvent was distilled away to give 8.08 g of ethyl trans-β-benzoylacrylate.

REFERENCE EXAMPLE

A mixture of 7.75 g of trans-β-benzoylacrylic acid, 25.8 ml of ethanol and 1.63 g of sulfuric acid was stirred at 62° C. for 3 hours. After cooling, the resultant was diluted with water and was then extracted with ethyl acetate. The ethyl acetate layer was washed with a saturated solution of $NaHCO_3$ and then with water and was dried with anhydrous magnesium sulfate. The solvent was distilled away to give 7.86 g of a mixture of ethyl trans-β-benzoylacrylate and ethyl β-benzoyl-α-ethoxypropionate (3 : 1 according to $^1H$ NMR analysis).

What we claim is:

1. A process for preparing trans-β-benzoylacrylic acid ester having the general formula (I):

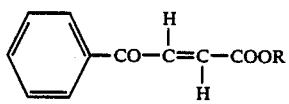 (I)

wherein R is an alkyl group or an aralkyl group, which comprises dealcoholizing β-benzoyl-α-alkoxypropionic acid ester having the general formula (II):

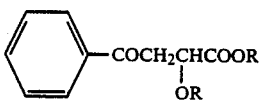 (II)

wherein R is as above, by removing from the reaction system an alcohol having the general formula (V):

ROH (V)

wherein R is as above, in the presence of an acid catalyst at a temperature of from 20° to 150° C. to give trans-β-benzoylacrylic acid ester having the general formula (I).

2. The process according to claim 1, wherein the removal of alcohol is carried out by distillation.

3. The process according to claim 1 or 2, wherein the acid catalyst is selected from a group consisting of sulfuric acid, hydrochloric acid, paratoluenesulfonic acid and boron trifluoride etherate.

4. The process according to claim 1 or 2, wherein, cis-β-benzoylacrylic acid ester having the general formula (IV):

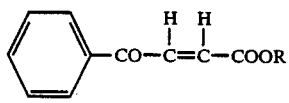 (IV)

wherein R is as defined above, coexists with the compound (II), and said compound (IV) is isomerized to the compound (I) by said acid catalyst in the course of the removal of the alcohol.

5. The process according to claim 4, wherein the compound (II) is present in a reaction mixture produced by the dehydration reaction of the trans-form, the cis-form or a mixture of the trans-form and the cis-form of β-benzoylacrylic acid having the formula (III):

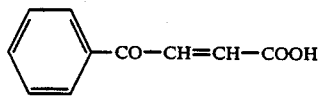 (III)

with an alcohol having the general formula (V):

ROH (V)

wherein R is as above, in the presence of said acid catalyst.

6. The process of claim 5, wherein produced water is removed with an azeotropic solvent.

7. The process according to claim 1, wherein the compound (II) is present in a reaction mixture produced by the dehydration reaction of the trans-form, the cis-form or a mixture of the trans-form and the cis-form of β-benzoylacrylic acid having the formula (III):

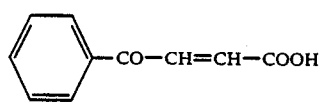 (III)

with an alcohol having the general formula (V):

ROH (V)

wherein R is as above, in the presence of said acid catalyst.

8. The process of claim 7, wherein produced water is removed with an azeotropic solvent.

9. A process for preparing trans-β-benzoylacrylic acid ester having the formula (I):

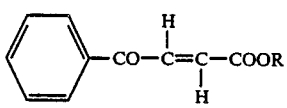 (I)

wherein R is an alkyl group or an aralkyl group, which comprises dehydrating the trans-form of a β-benzoylacrylic acid having the formula (III):

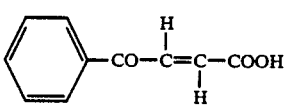 (III)

with an alcohol having the formula (V):

ROH (V)

wherein R is as defined above, in the presence of an acid catalyst to form a mixture of trans-β-benzoylacrylic acid ester having the formula (I) and β-benzoyl-α-alkoxypropionic acid ester having the formula (II):

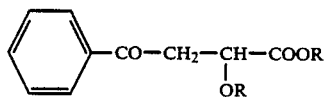 (II)

and removing from the reaction system said alcohol having the formula (V) in the presence of said acid catalyst at a temperature of from 20° C. to 150° C. to dealcoholize said β-benzoyl-α-alkoxypropionic acid ester and to result in converting said β-benzoyl-α-alkoxypropionic acid ester into trans-β-benzoylacrylic acid ester having the formula (I).

10. The process of claim 9, wherein produced water is removed with an azeotropic solvent.

11. A process for preparing trans-β-benzoylacrylic acid ester having the formula (I):

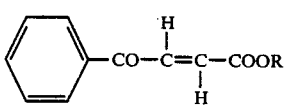 (I)

wherein R is an alkyl group or an aralkyl group, which comprises dehydrating the cis-form of a β-benzoylacrylic acid having the formula (III''):

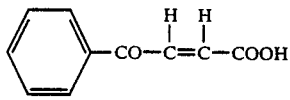 (III'')

or a mixture of the cis-form having the formula (III'') and the trans-form of a β-benzoylacrylic acid having the formula (III):

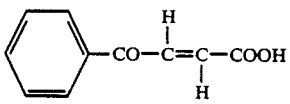 (III)

with an alcohol having the formula (V):

ROH      (V)

wherein R is defined above, in the presence of an acid catalyst to form a mixture of trans-β-benzoylacrylic acid ester having the formula (I), β-benzoyl-α-alkoxypropionic acid ester having the formula (II):

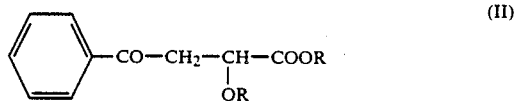 (II)

and a cis-β-benzoylacrylic acid ester having the formula (IV):

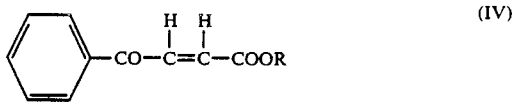 (IV)

and removing said alcohol form the reaction system in the presence of said acid catalyst at a temperature of from 20° C. to 150° C. to dealcoholize said β-benzoyl-α-alkoxypropionic acid ester having the formula (II) and to result in converting said β-benzoyl-α-alkoxypropionic acid ester into trans-β-benzoylacrylic acid ester having the formula (I), and to result in isomerizing cis-β-benzoylacrylic acid ester having the formula (IV) into said trans-β-benzoylacrylic acid ester having the formula (I).

* * * * *

UNITED STATES PATENT AND TRADEMARK OFFICE
CERTIFICATE OF CORRECTION

PATENT NO. : 4,994,600

DATED : February 19, 1991

INVENTOR(S) : Satomi TAKAHASHI et al

It is certified that error appears in the above-identified patent and that said Letters Patent is hereby corrected as shown below:

On the cover page, Item [75], third line, "Namito Yoshio" should read -- Yoshio Namito --; and On the cover page, Item [73], "Kanegafuchi, Kagaku, Kogyo, Kabushiki, Kaisha" should read -- Kanegafuchi Kagaku Kogyo Kabushiki Kaisha --.

Signed and Sealed this

Twenty-ninth Day of September, 1992

Attest:

DOUGLAS B. COMER

*Attesting Officer*     *Acting Commissioner of Patents and Trademarks*